US007917377B2

(12) United States Patent
Rao et al.

(10) Patent No.: US 7,917,377 B2
(45) Date of Patent: Mar. 29, 2011

(54) PATIENT DATA MINING FOR AUTOMATED COMPLIANCE

(75) Inventors: R. Bharat Rao, Berwyn, PA (US); Sathyakama Sandilya, Cranbury, NJ (US); Radu Stefan Niculescu, Pittsburgh, PA (US); Harm J. Scherpbier, Fort Washington, PA (US); Thomas R. Warrick, Wayne, PA (US)

(73) Assignees: Siemens Medical Solutions USA, Inc., Malvern, PA (US); Siemens Corporation, Iselin, NJ (US)

( * ) Notice: Subject to any disclaimer, the term of this patent is extended or adjusted under 35 U.S.C. 154(b) by 1401 days.

(21) Appl. No.: 10/287,054

(22) Filed: Nov. 4, 2002

(65) Prior Publication Data

US 2003/0125984 A1 Jul. 3, 2003

Related U.S. Application Data

(60) Provisional application No. 60/335,542, filed on Nov. 2, 2001.

(51) Int. Cl.
*G06F 19/00* (2006.01)
*G06Q 50/00* (2006.01)

(52) U.S. Cl. ............................................. 705/3; 705/2
(58) Field of Classification Search .................. 705/2–3
See application file for complete search history.

(56) References Cited

U.S. PATENT DOCUMENTS

| | | | | |
|---|---|---|---|---|
| 4,946,679 A | | 8/1990 | Thys-Jacobs | |
| 5,307,262 A | * | 4/1994 | Ertel | 705/2 |
| 5,359,509 A | * | 10/1994 | Little et al. | 705/2 |
| 5,365,425 A | * | 11/1994 | Torma et al. | 705/2 |
| 5,508,912 A | * | 4/1996 | Schneiderman | 705/3 |
| 5,544,044 A | * | 8/1996 | Leatherman | 705/3 |
| 5,557,514 A | * | 9/1996 | Seare et al. | 705/2 |
| 5,619,991 A | | 4/1997 | Sloane | |
| 5,652,842 A | * | 7/1997 | Siegrist et al. | 705/2 |
| 5,657,255 A | | 8/1997 | Fink et al. | |
| 5,664,109 A | * | 9/1997 | Johnson et al. | 705/3 |
| 5,669,877 A | * | 9/1997 | Blomquist | 604/67 |
| 5,706,441 A | * | 1/1998 | Lockwood | 705/3 |
| 5,724,379 A | * | 3/1998 | Perkins et al. | 705/3 |
| 5,737,539 A | | 4/1998 | Edelson et al. | |
| 5,811,437 A | | 9/1998 | Singh et al. | |
| 5,832,450 A | * | 11/1998 | Myers et al. | 705/3 |

(Continued)

FOREIGN PATENT DOCUMENTS

EP 0 917 078 A1 10/1997

(Continued)

OTHER PUBLICATIONS

Kassirer, The Use and Abuse of Practice Profiles, Mar. 3, 1994. The New England Journal of Medicine, vol. 330:634-636.*

(Continued)

*Primary Examiner* — Luke Gilligan
*Assistant Examiner* — Tran Nguyen
(74) *Attorney, Agent, or Firm* — Joshua B. Ryan

(57) ABSTRACT

A technique is provided for automatically generating performance measurement information. At least some of the obtained performance measurement information may be derived from unstructured data sources, such as free text physician notes, medical images, and waveforms. The performance measurement may be sent to a health care accreditation organization. The health care accreditation organization can use the performance measurement to evaluate a health care provider for its quality of patient care. Alternatively, performance measurement information can be provided directly to consumers.

56 Claims, 4 Drawing Sheets

U.S. PATENT DOCUMENTS

| | | | | |
|---|---|---|---|---|
| 5,835,897 | A * | 11/1998 | Dang | 705/2 |
| 5,845,253 | A | 12/1998 | Rensimer et al. | |
| 5,899,998 | A | 5/1999 | McGauley et al. | |
| 5,924,073 | A * | 7/1999 | Tyuluman et al. | 705/2 |
| 5,935,060 | A | 8/1999 | Iliff | |
| 5,939,528 | A | 8/1999 | Clardy et al. | |
| 6,076,088 | A * | 6/2000 | Paik et al. | 1/1 |
| 6,078,894 | A * | 6/2000 | Clawson et al. | 705/11 |
| 6,081,786 | A | 6/2000 | Barry et al. | |
| 6,083,693 | A | 7/2000 | Nandabalan et al. | |
| 6,108,635 | A | 8/2000 | Herren et al. | |
| 6,128,620 | A * | 10/2000 | Pissanos et al. | 707/102 |
| 6,151,581 | A * | 11/2000 | Kraftson et al. | 705/3 |
| 6,196,970 | B1 | 3/2001 | Brown | |
| 6,253,186 | B1 * | 6/2001 | Pendleton, Jr. | 705/2 |
| 6,259,890 | B1 | 7/2001 | Driscoll et al. | |
| 6,266,645 | B1 * | 7/2001 | Simpson | 705/3 |
| 6,272,472 | B1 | 8/2001 | Danneels et al. | |
| 6,322,502 | B1 | 11/2001 | Schoenberg et al. | |
| 6,338,042 | B1 * | 1/2002 | Paizis | 705/11 |
| 6,381,576 | B1 * | 4/2002 | Gilbert | 705/2 |
| 6,468,210 | B1 | 10/2002 | Iliff | |
| 6,484,144 | B2 | 11/2002 | Martin et al. | |
| 6,529,876 | B1 | 3/2003 | Dart et al. | |
| 6,551,243 | B2 | 4/2003 | Bocionek et al. | |
| 6,551,266 | B1 | 4/2003 | Davis, Jr. | |
| 6,611,846 | B1 | 8/2003 | Stoodley | |
| 6,641,532 | B2 | 11/2003 | Iliff | |
| 6,645,959 | B1 | 11/2003 | Bakker-Arkema et al. | |
| 6,678,669 | B2 | 1/2004 | Lapointe et al. | |
| 8,754,855 | | 6/2004 | Segal | |
| 6,804,656 | B1 | 10/2004 | Rosenfeld et al. | |
| 8,802,810 | | 10/2004 | Clamiello et al. | |
| 6,826,536 | B1 * | 11/2004 | Forman | 705/4 |
| 6,839,678 | B1 | 1/2005 | Schmidt et al. | |
| 6,903,194 | B1 | 6/2005 | Sato et al. | |
| 6,915,254 | B1 * | 7/2005 | Heinze et al. | 704/9 |
| 6,915,266 | B1 * | 7/2005 | Saeed et al. | 705/2 |
| 6,941,271 | B1 | 9/2005 | Soong | |
| 6,988,075 | B1 | 1/2006 | Hacker | |
| 7,058,658 | B2 | 6/2006 | Mentzer | |
| 7,130,457 | B2 | 10/2006 | Kaufman et al. | |
| 7,307,543 | B2 | 12/2007 | Rosenfeld et al. | |
| 2001/0011243 | A1 | 8/2001 | Dembo et al. | |
| 2001/0032195 | A1 * | 10/2001 | Graichen et al. | 705/400 |
| 2001/0041991 | A1 | 11/2001 | Segal et al. | |
| 2001/0051882 | A1 | 12/2001 | Murphy et al. | |
| 2002/0002474 | A1 | 1/2002 | Michelson et al. | |
| 2002/0010597 | A1 | 1/2002 | Mayer et al. | |
| 2002/0026332 | A1 | 2/2002 | Snowden et al. | |
| 2002/0032581 | A1 | 3/2002 | Reitberg | |
| 2002/0035316 | A1 | 3/2002 | Drazen | |
| 2002/0077853 | A1 | 6/2002 | Boru et al. | |
| 2002/0082480 | A1 | 6/2002 | Riff et al. | |
| 2002/0087361 | A1 * | 7/2002 | Benigno et al. | 705/3 |
| 2002/0099570 | A1 | 7/2002 | Knight | |
| 2002/0123905 | A1 * | 9/2002 | Goodroe et al. | 705/2 |
| 2002/0138492 | A1 | 9/2002 | Kil | |
| 2002/0138524 | A1 * | 9/2002 | Ingle et al. | 707/530 |
| 2002/0143577 | A1 * | 10/2002 | Shiffman et al. | 705/2 |
| 2002/0165736 | A1 * | 11/2002 | Tolle et al. | 705/3 |
| 2002/0173990 | A1 | 11/2002 | Marasco | |
| 2002/0177759 | A1 | 11/2002 | Schoenberg et al. | |
| 2003/0028401 | A1 | 2/2003 | Kaufman et al. | |
| 2003/0046114 | A1 | 3/2003 | Davies et al. | |
| 2003/0050794 | A1 * | 3/2003 | Keck | 705/2 |
| 2003/0108938 | A1 | 6/2003 | Pickar et al. | |
| 2003/0120133 | A1 | 6/2003 | Rao et al. | |
| 2003/0120134 | A1 | 6/2003 | Rao et al. | |
| 2003/0120458 | A1 | 6/2003 | Rao et al. | |
| 2003/0120514 | A1 | 6/2003 | Rao et al. | |
| 2003/0125985 | A1 | 7/2003 | Rao et al. | |
| 2003/0125988 | A1 | 7/2003 | Rao et al. | |
| 2003/0126101 | A1 | 7/2003 | Rao et al. | |
| 2003/0130871 | A1 | 7/2003 | Rao et al. | |
| 2003/0208382 | A1 | 11/2003 | Westfall | |
| 2004/0078216 | A1 | 4/2004 | Toto | |
| 2005/0187794 | A1 | 8/2005 | Kimak | |
| 2006/0064415 | A1 | 3/2006 | Guyon et al. | |

FOREIGN PATENT DOCUMENTS

| | | |
|---|---|---|
| JP | 11328073 A | 11/1999 |
| JP | 2001297157 A | 10/2001 |
| WO | 98/39720 | 9/1998 |
| WO | 01/82173 A1 | 11/2001 |

OTHER PUBLICATIONS

Chen, Do."America's Best Hospitals" Perform Better for Acute Myocardial Infarctions?, Jan. 28, 1999, The New England Journal of Medicine, vol. 340 No. 4:286-292.*

Hofer, The Unreliability of Individual Physician "Report Cards" for Assessing the Costs and Quality of Care of a Chronic Disease, Jun. 9, 1999, JAMA, vol. 281 No. 22:2098-2105.*

Grimes, Structure, Models and Meaning, Is "unstructured" data merely unmodeled?, Mar. 1, 2005, Intelligent Enterprise, http://www.intelligententerprise.com/showArticle.jhtml?articleID=59301538.*

Berkus, "Unstructured Data" as an Oxymoron, Sep. 1, 2005, ITtoolbox Blogs, http://blogs.ittoolbox.com/database/soup/archives/unstructured-data-as-an-oxymoron-5588.*

Larsen, Fast and effective text mining using linear-time document clustering, 1999, ACM Press, Conference on Knowledge Discovery in Data, Proceedings of the fifth ACM SIGKDD international conference on Knowledge discovery and data mining, p. 16-22.*

Mitchell, Machine learning and data mining, Nov. 1999, ACM Press, Communications of the ACM, vol. 42, Issue 11, p. 30-36.*

Duda, Pattern Classification, 2001, John Wiley & Sons, Inc., p. vii-xx, Chapter I.*

Hudson, The feasibility of using automated data to assess guideline-concordant care for schizophrenia, Dec. 4, 1999, Journal of Medical Systems, vol. 23, No. 4, p. 299-307.*

PR Newswire, Diabetes Health Management Award Honors Mayo Clinic's Zimmerman, Sep. 25, 2000.*

Hudson, CAATS and compliance, Apr. 1998, The Internal Auditor, vol. 55, No. 2, p. 25.*

Mills, Computer technology of the not-too-distant future, Sep. 1993, Medical Laboratory Observer, vol. 25, No. 9. p. 78.*

Hudson, The Feasibility of Using Automated Data to Assess Guideline-Concordant Care for Schizophrenia, Journal of Medical Systems, vol. 23, No. 4, 1999, p. 299-307.*

Ramana Rao, "From Unstructured Data to Actionable Intelligence", IT Pro, Nov./Dec. 2003, pp. 29-35.

Guidance for Institutional Review Boards and Clinical Investigators 1998 Update, Sep. 1998, U.S. Food and Drug Administration.

King et al., MEDUS/A: Distributing Database Management for Medical Research, Proceedings of Computer Networks Compcon 82, Sep. 20-23, 1982, pp. 635-642.

Boxwala et al., "Architecture for a Multipurpose Guideline Execution Engine", Proc. AMIA Symp 1999, pp. 701-705.

* cited by examiner

ACUTE MYOCARDIAL INFARCTION (AMI)
PERFORMANCE MEASURE - AMI1

SELECT ALL PATIENTS
   WHERE DISEASE = AMI
   AGE ≥ 18
   CONTRAINDICATION TO ASPIRIN = 'N'
   TRANSFERRED ON DAY OF ARRIVAL = 'N'
   RECEIVED IN TRANSFER = 'N'
   DISCHARGED ON DAY OF ARRIVAL = 'N'
   EXPIRED ON DAY OF ARRIVAL = 'N'
   LEFT AGAINST MEDICAL ADVICE = 'N'

FIG. 3

PATIENT DATA MINING FOR AUTOMATED COMPLIANCE

CROSS REFERENCE TO RELATED APPLICATIONS

This application claims the benefit of U.S. Provisional Application Ser. No. 60/335,542, filed on Nov. 2, 2001, which is incorporated by reference herein in its entirety.

FIELD OF THE INVENTION

The present invention relates to medical information processing systems, and, more particularly to a computerized system and method for providing automated performance measurement information for health care organizations.

BACKGROUND OF THE INVENTION

Health care organizations need to generate various types of performance measurement information to determine how well they are progressing over time. Health care organizations typically use this information to determine areas of excellence within their organizations as well as those areas that need improvement. Performance measurement information provides an objective basis for planning and making budgeting decisions. In addition, performance measurement information can be used to demonstrate accountability to the public and to back up claims of quality. Frequently, performance measurement information is provided to accreditation organizations for compliance purposes.

The Joint Commission on Accreditation of Healthcare Organizations (JCAHO), an organization that accredits more than 4,700 hospitals nationwide, requires that participating hospitals provide certain types of performance measurement information. For example, JCAHO requires that participating hospitals provide information regarding patients treated for acute myocardial infarction (AMI). As one example of the type of information that must be provided, hospitals are required to indicate whether an AMI patient without aspirin contraindication received aspirin within 24 hours before or after hospital arrival. Because it is believed that early treatment with aspirin markedly reduces mortality for AMI, JCAHO requires hospitals to report this information.

Currently, performance measurement information must be collected from a myriad of structured and unstructured data sources to comply with accreditation requests. For example, it may be necessary to access numerous different databases, each with its own peculiar format. Worse, physician notes may have to be consulted. These notes usually are nothing more than free text dictations, and it may be very difficult to sift through the notes to gather the necessary information. As a result, the effort taken to collect this information is usually time consuming, expensive, and error prone. Furthermore, usually only a small sample of patient data can be supplied.

Given the importance of collecting accurate performance measurement information, it would be desirable and highly advantageous to provide new techniques for automatically generating performance measurement information for health care organizations.

SUMMARY OF THE INVENTION

The present invention provides a technique for automatically generating performance measurement information for health care organizations.

In various embodiments of the present invention, a method is provided that includes formulating a query based on a specified performance measurement category. This query is then executed to obtain performance measurement information. At least some of the obtained performance measurement information may be derived from unstructured data sources, such as free text physician notes.

The performance measurement information can be outputted. The performance measurement information may be sent to a health care accreditation organization. An example of a health care accreditation organization is the Joint Commission on Accreditation of Health Care Organizations (JCAHO).

Performance measurement information can include patient information from a health care provider being evaluated. For example, a health care accreditation organization may evaluate a hospital for its quality of care in treating heart attack patients. This patient information may include clinical information, financial information, and demographic information.

The obtained performance measurement information may be sampled from a patient population. Alternatively, it may be obtained for an entire patient population.

Performance measurement information may be generated by a health care provider, third party service provider, or an accreditation organization. The performance measurement information may be made available using a network, such as, for example, the Internet.

In various embodiments, an evaluation score of a health care provider may be calculated using the obtained performance measurement information. This evaluation score may be outputted for evaluating health care providers. Health care consumers may have the opportunity to view or download evaluation information via the Internet. Health care providers may be ranked according to the evaluation scores. Such rankings may be done for various performance measurement categories.

These and other aspects, features and advantages of the present invention will become apparent from the following detailed description of preferred embodiments, which is to be read in connection with the accompanying drawings.

BRIEF DESCRIPTION OF THE DRAWINGS

FIG. 3 shows an exemplary query for selecting performance measurement information.

DESCRIPTION OF PREFERRED EMBODIMENTS

To facilitate a clear understanding of the present invention, illustrative examples are provided herein which describe certain aspects of the invention. However, it is to be appreciated that these illustrations are not meant to limit the scope of the invention, and are provided herein to illustrate certain concepts associated with the invention.

It is also to be understood that the present invention may be implemented in various forms of hardware, software, firmware, special purpose processors, or a combination thereof.

Preferably, the present invention is implemented in software as a program tangibly embodied on a program storage device. The program may be uploaded to, and executed by, a machine comprising any suitable architecture. Preferably, the machine is implemented on a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the program (or combination thereof) which is executed via the operating system. In addition, various other peripheral devices may be connected to the computer platform such as an additional data storage device and a printing device.

It is to be understood that, because some of the constituent system components and method steps depicted in the accompanying figures are preferably implemented in software, the actual connections between the system components (or the process steps) may differ depending upon the manner in which the present invention is programmed.

Figure 1:
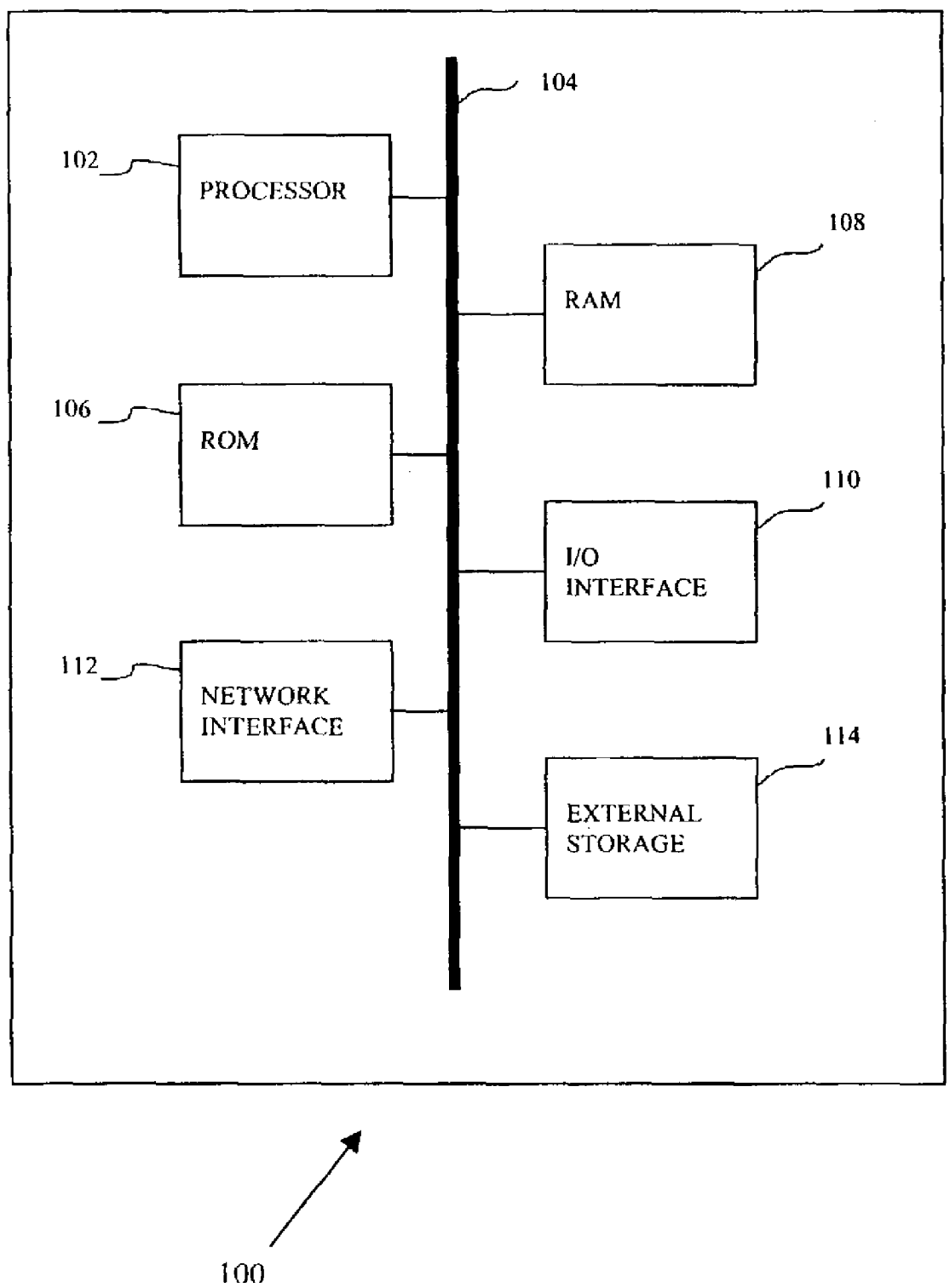
FIG. 1 is a block diagram of a computer processing system to which the present invention may be applied according to an embodiment of the present invention.

FIG. 1 is a block diagram of a computer processing system 100 to which the present invention may be applied according to an embodiment of the present invention. The system 100 includes at least one processor (hereinafter processor) 102 operatively coupled to other components via a system bus 104. A read-only memory (ROM) 106, a random access memory (RAM) 108, an I/O interface 110, a network interface 112, and external storage 114 are operatively coupled to the system bus 104. Various peripheral devices such as, for example, a display device, a disk storage device (e.g., a magnetic or optical disk storage device), a keyboard, and a mouse, may be operatively coupled to the system bus 104 by the I/O interface 110 or the network interface 112.

The computer system 100 may be a standalone system or be linked to a network via the network interface 112. The network interface 112 may be a hard-wired interface. However, in various exemplary embodiments, the network interface 112 can include any device suitable to transmit information to and from another device, such as a universal asynchronous receiver/transmitter (UART), a parallel digital interface, a software interface or any combination of known or later developed software and hardware. The network interface may be linked to various types of networks, including a local area network (LAN), a wide area network (WAN), an intranet, a virtual private network (VPN), and the Internet.

The external storage 114 may be implemented using a database management system (DBMS) managed by the processor 102 and residing on a memory such as a hard disk. However, it should be appreciated that the external storage 114 may be implemented on one or more additional computer systems. For example, the external storage 114 may include a data warehouse system residing on a separate computer system.

Those skilled in the art will appreciate that other alternative computing environments may be used without departing from the spirit and scope of the present invention.

Figure 2:
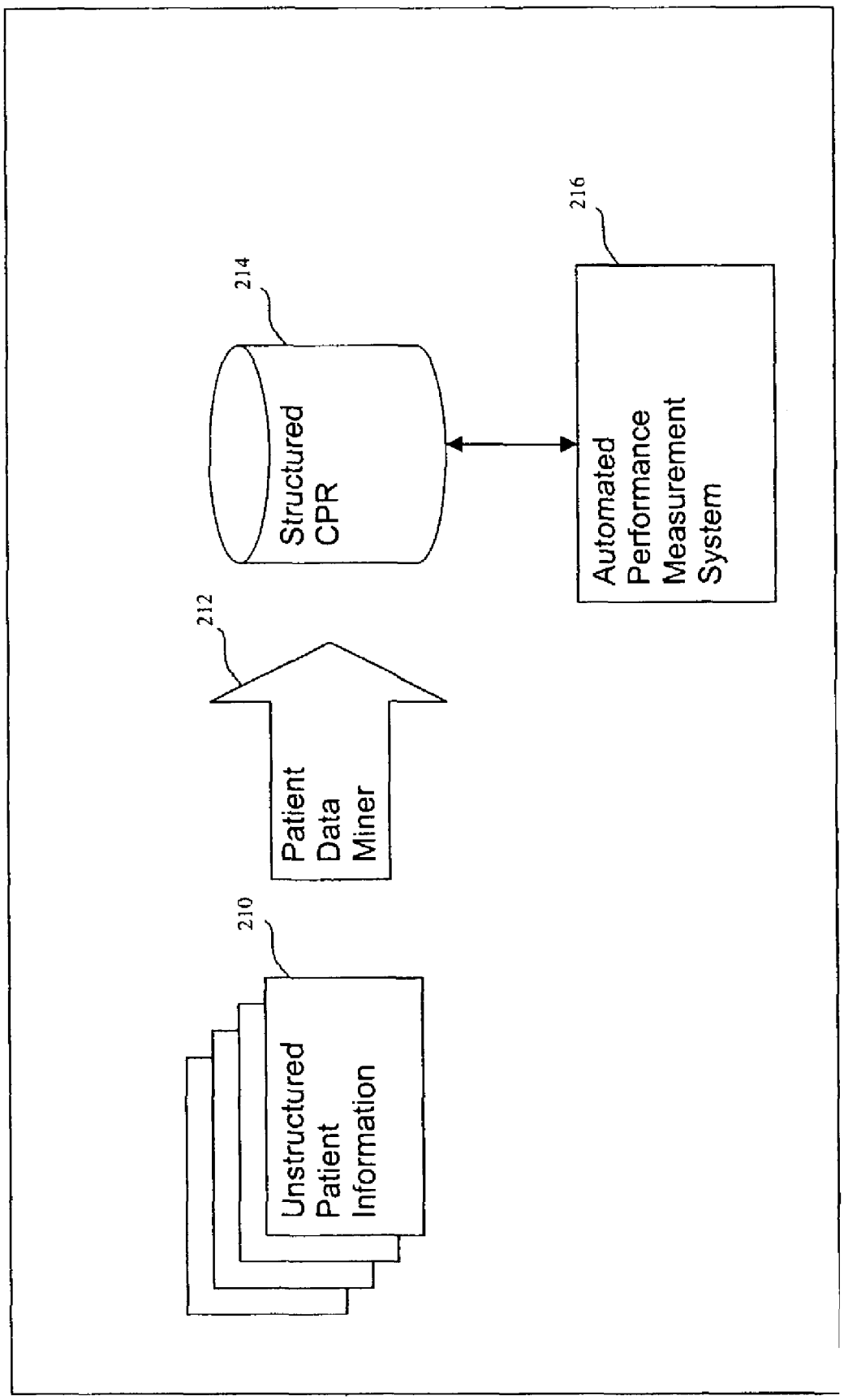
FIG. 2 shows an exemplary automated performance measurement information system in accordance with an embodiment of the present invention.

Referring to FIG. 2, an automated performance measurement system 216 is illustrated. The automated performance measurement system 216 is shown connected to a data repository which contains structured patient information collected from one or more health care organization. This data repository is called a structured clinical patient record (CPR) 214. The CPR 214 is shown connected to a data miner 212 which mines high-quality structured clinical information from unstructured patient information 210.

Preferably, the structured CPR 214 is populated with patient information using data mining techniques described in "Patient Data Mining," by Rao et al., copending U.S. Published Patent Application No. 2003/0126101, filed herewith, which is incorporated by reference herein in its entirety.

That disclosure teaches a data mining framework for mining high-quality structured clinical information. The data mining framework includes a data miner that mines medical information from a computerized patient record based on domain-specific knowledge contained in a knowledge base. The data miner includes components for extracting information from the computerized patient record, combining all available evidence in a principled fashion over time, and drawing inferences from this combination process. The mined medical information is stored in a structured computerized patient record.

The extraction component deals with gleaning small pieces of information from each data source regarding a patient, which are represented as probabilistic assertions about the patient at a particular time. These probabilistic assertions are called elements. The combination component combines all the elements that refer to the same variable at the same time period to form one unified probabilistic assertion regarding that variable. These unified probabilistic assertions are called factoids. The inference component deals with the combination of these factoids, at the same point in time and/or at different points in time, to produce a coherent and concise picture of the progression of the patient's state over time. This progression of the patient's state is called a state sequence.

An individual model of the state of a patient may be built. The patient state is simply a collection of variables that one may care about relating to the patient. The information of interest may include a state sequence, i.e., the value of the patient state at different points in time during the patient's treatment.

Each of the above components uses detailed knowledge regarding the domain of interest, such as, for example, a disease of interest. This domain knowledge base can come in two forms. It can be encoded as an input to the system, or as programs that produce information that can be understood by the system. The part of the domain knowledge base that is input to the present form of the system may also be learned from data.

Domain-specific knowledge for mining the data sources may include institution-specific domain knowledge. For example, this may include information about the data available at a particular hospital, document structures at a hospital, policies of a hospital, guidelines of a hospital, and any variations of a hospital.

The domain-specific knowledge may also include disease-specific domain knowledge. For example, the disease-specific domain knowledge may include various factors that influence risk of a disease, disease progression information, complications information, outcomes and variables related to a disease, measurements related to a disease, and policies and guidelines established by medical bodies.

As mentioned, the extraction component takes information from the CPR to produce probabilistic assertions (elements) about the patient that are relevant to an instant in time or time period. This process is carried out with the guidance of the domain knowledge that is contained in the domain knowledge base. The domain knowledge required for extraction is generally specific to each source.

Extraction from a text source may be carried out by phrase spotting, which requires a list of rules that specify the phrases of interest and the inferences that can be drawn therefrom. For example, if there is a statement in a doctor's note with the words "There is evidence of metastatic cancer in the liver," then, in order to infer from this sentence that the patient has cancer, a rule is needed that directs the system to look for the phrase "metastatic cancer," and, if it is found, to assert that the patient has cancer with a high degree of confidence (which, in the present embodiment, translates to generate an element with name "Cancer", value "True" and confidence 0.9).

The data sources include structured and unstructured information. Structured information may be converted into standardized units, where appropriate. Unstructured information may include ASCII text strings, image information in DICOM (Digital Imaging and Communication in Medicine) format, and text documents partitioned based on domain knowledge. Information that is likely to be incorrect or missing may be noted, so that action may be taken. For example, the mined information may include corrected information, including corrected ICD-9 diagnosis codes.

Extraction from a database source may be carried out by querying a table in the source, in which case, the domain knowledge needs to encode what information is present in which fields in the database. On the other hand, the extraction process may involve computing a complicated function of the information contained in the database, in which case, the domain knowledge may be provided in the form of a program that performs this computation whose output may be fed to the rest of the system.

Extraction from images, waveforms, etc., may be carried out by image processing or feature extraction programs that are provided to the system.

Combination includes the process of producing a unified view of each variable at a given point in time from potentially conflicting assertions from the same/different sources. In various embodiments of the present invention, this is performed using domain knowledge regarding the statistics of the variables represented by the elements ("prior probabilities").

Inference is the process of taking all the factoids that are available about a patient and producing a composite view of the patient's progress through disease states, treatment protocols, laboratory tests, etc. Essentially, a patient's current state can be influenced by a previous state and any new composite observations.

The domain knowledge required for this process may be a statistical model that describes the general pattern of the evolution of the disease of interest across the entire patient population and the relationships between the patient's disease and the variables that may be observed (lab test results, doctor's notes, etc.). A summary of the patient may be produced that is believed to be the most consistent with the information contained in the factoids, and the domain knowledge.

For instance, if observations seem to state that a cancer patient is receiving chemotherapy while he or she does not have cancerous growth, whereas the domain knowledge states that chemotherapy is given only when the patient has cancer, then the system may decide either: (1) the patient does not have cancer and is not receiving chemotherapy (that is, the observation is probably incorrect), or (2) the patient has cancer and is receiving chemotherapy (the initial inference—that the patient does not have cancer—is incorrect); depending on which of these propositions is more likely given all the other information. Actually, both (1) and (2) may be concluded, but with different probabilities.

As another example, consider the situation where a statement such as "The patient has metastatic cancer" is found in a doctor's note, and it is concluded from that statement that <cancer=True (probability=0.9)>. (Note that this is equivalent to asserting that <cancer=True (probability=0.9), cancer=unknown (probability=0.1)>).

Now, further assume that there is a base probability of cancer <cancer=True (probability=0.35), cancer=False (probability=0.65)> (e.g., 35% of patients have cancer). Then, we could combine this assertion with the base probability of cancer to obtain, for example, the assertion <cancer=True (probability=0.93), cancer=False (probability=0.07)>.

Similarly, assume conflicting evidence indicated the following:
1. <cancer=True (probability=0.9), cancer=unknown probability=0.1)>
2. <cancer=False (probability=0.7), cancer=unknown (probability=0.3)>
3. <cancer=True (probability=0.1), cancer unknown (probability=0.9)> and
4. <cancer=False (probability=0.4), cancer unknown (probability=0.6)>.

In this case, we might combine these elements with the base probability of cancer <cancer=True (probability=0.35), cancer=False (probability=0.65)> to conclude, for example, that <cancer=True (prob=0.67), cancer=False (prob=0.33)>.

Referring again to FIG. 2, the automated performance measurement system 216 can be configured to generate performance measurement information for one or more performance measurement category. Once a performance measurement category is selected, a query can be formulated based on the selected performance measurement category.

The query is then executed to obtain performance measurement information. At least some of the obtained performance measurement information may be derived from unstructured data sources, such as, for example, free text, medical images and waveforms.

An exemplary query is shown in FIG. 3. In accordance with JCAHO accreditation requirements, hospitals must indicate whether an acute myocardial infarction (AMI) patient without aspirin contraindication received aspirin within 24 hours before or after hospital arrival. The query shows that all AMI patients are selected except those excluded under JCAHO guidelines. JCAHO excludes patients who are less than 18 years of age, transferred to another acute care hospital on day of arrival, received in transfer from another hospital, discharged on day of arrival, expired on day of arrival, left against medical advice on day of arrival, or have aspirin contraindications.

It should be appreciated that the query shown in FIG. 3 is shown for illustrative purposes only. Further, it is to be appreciated that the actual performance measurement categories used to implement the present invention can relate to any type of performance measurement, including those related to any aspect of health care quality, safety, or compliance with standards.

As mentioned previously, the performance measurement information can be sent to a health care accreditation organization such as JCAHO. The obtained performance measurement information may be sampled or obtained for an entire patient population.

Performance measurement information may be generated by a health care provider, third party service provider, or an accreditation organization. The performance measurement information may be made available using any suitable network.

In order to empower health care consumers, an evaluation score of a health care provider may be determined using the obtained performance measurement information. Consumers may view or download this evaluation information via the Internet, for example. Health care providers may be ranked according to the evaluation scores. Such rankings may be done for various performance measurement categories. For example, hospitals in a particular geographic area may be ranked according to quality of care in treating prostate cancer. There may be another list that ranks hospitals nationwide for quality of care in treating infectious diseases, etc.

Figure 4:
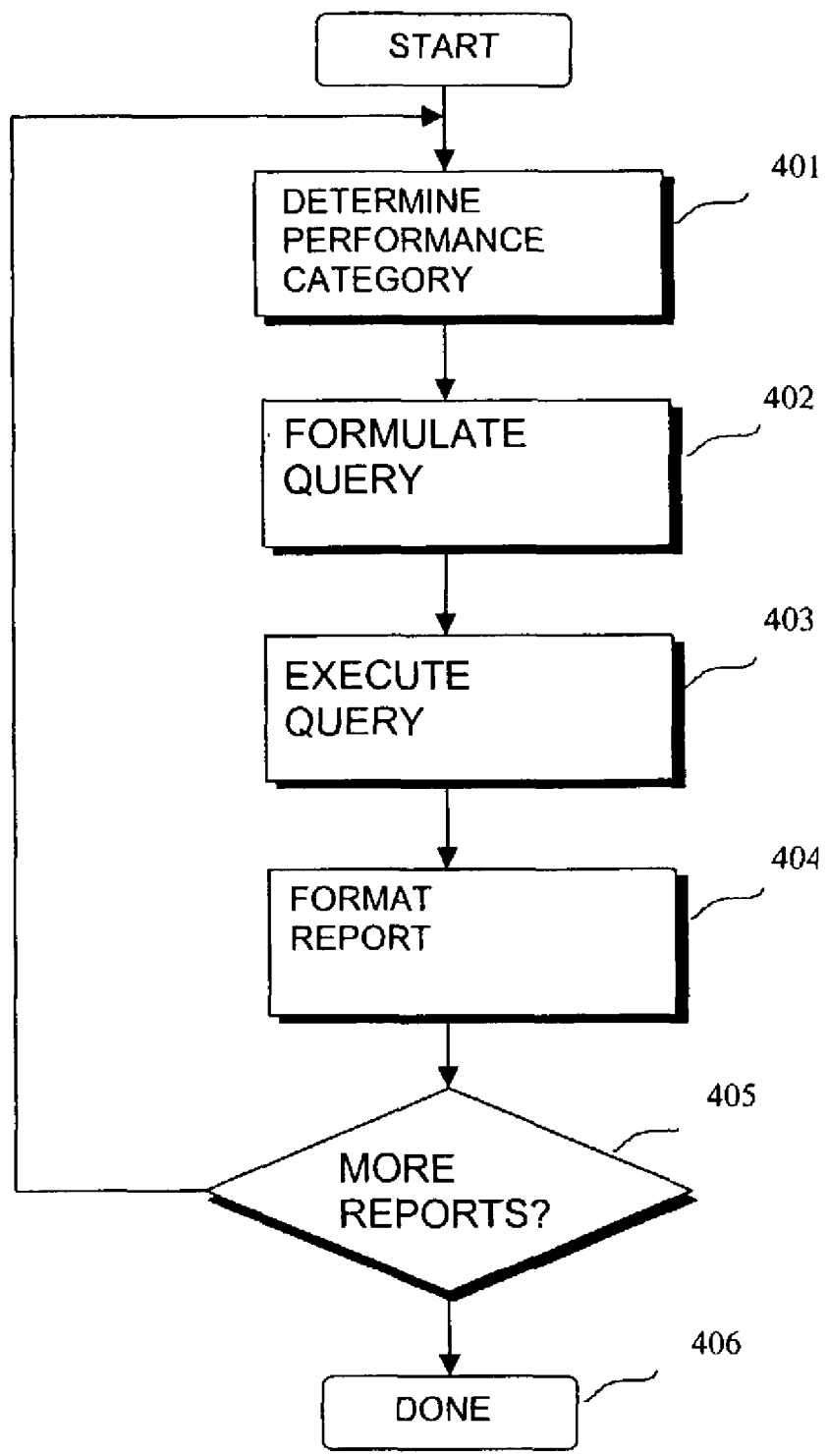
FIG. 4 shows a flow diagram outlining an exemplary technique for automatically generating performance measurement information.

Referring to FIG. 4, a flow diagram outlining an exemplary technique for automatically generating performance measurement information is illustrated. Beginning at step 401, a performance measurement category is selected. This may involve selecting from among several performance measurement categories that are presented to a user. (Of course, this step may be skipped if there is only one performance measurement category).

In step 402, a query is formulated based on the selected performance measurement category. (This may involve formulating a query such as the one shown in FIG. 3). The query may be formulated to select all patients for the performance measurement category or only a sample of them. The particular sample size may be input as a parameter value.

In step 402, the query is executed to obtain performance measurement information. At least some of the obtained performance measurement information may have been derived from unstructured information. Preferably, this information resides in a structured data repository that is populated using mined unstructured patient information, as described in "Patient Data Mining," by Rao et al., copending U.S. Published Patent Application No. 2003/0126101.

In step 404, a compliance report is formatted. While this step involves creating a report, it should be appreciated that there are many other ways to output performance measurement information. For instance, the performance measurement information may be output to a magnetic or optical disc, electronically transmitted, or displayed upon a screen.

In step 405, a determination is made as to whether any more reports are to be generated. If there are, then control returns back to step 401; otherwise, control continues to step 406 where the operation stops.

As shown in FIGS. 1-4, this invention is preferably implemented using a general purpose computer system. However the systems and methods of this invention can be implemented using any combination of one or more programmed general purpose computers, programmed microprocessors or micro-controllers and peripheral integrated circuit elements, ASIC or other integrated circuits, digital signal processors, hardwired electronic or logic circuits such as discrete element circuits, programmable logic devices such as a PLD, PLA, FPGA or PAL, or the like. In general, any device capable of implementing a finite state machine that is in turn capable of implementing the flowchart shown in FIG. 3 can be used to implement this system.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method for automatically generating performance measurement information for health care organizations, the method comprising:
mining, with a machine, free text, the mining on the free text comprising mining for health care data related to a health care guideline for a patient, the mining using medical knowledge, the medical knowledge associated with the health care guideline, the free text being stored physician notes, the mining comprising:
gleaning, as part of the mining for the patient, a plurality of pieces of evidence about the patient including at least one of the pieces being from the free text;
using, as part of the mining, probabilistic information, the probabilistic information comprising chances of occurrence for possible values of a variable being mined for the patient, the possible values being derived from the pieces of evidence such that a plurality of possible values and respective chances are provided for the variable;
calculating, as part of the mining, the chances from probabilities assigned to the pieces of evidence from the free text for the patient, the probabilities being less than 100% and greater than 0%;
as part of the mining, assigning, as the health care data for the variable for the patient, a value for the variable with the chance of occurrence greater than other chances for the possible values for the variable, the value being different than the respective chance;
populating, as part of the mining, a data source with at least some health care data mined from the free text, a structure of the mined data in the data source being different from a structure of the free text so that compliance querying may be performed using the data source, the structure of the mined data in the data source comprising the at least some health care data for the variable separate from the free text;
querying, with the machine executing a query script defining a plurality of constraints and formulated by the machine, the data source having the at least some data populated from the free text of the stored physician notes, the querying based on the health care guideline; and
outputting performance measurement information indicating a level of compliance with the health care guideline based on the querying.

2. The method of claim 1 further comprising:
calculating an evaluation score of a health care provider from the performance measurement information; and
outputting the evaluation score.

3. The method of claim 2 wherein outputting the evaluation scores comprises outputting the evaluation scores to consumers via the Internet.

4. The method of claim 3 wherein outputting the evaluation score comprises outputting a ranking of health care providers.

5. The method of claim 4 wherein outputting the evaluation score comprises ranking the health care providers in different performance measurement categories.

6. The method of claim 1 wherein mining comprises mining a plurality of patient records associated with a health care provider and wherein outputting comprises outputting patient information for the health care provider being evaluated.

7. The method of claim 6 wherein outputting comprises outputting the patient information including at least one of clinical information, financial information, demographic information and combinations thereof.

8. The method of claim 1 wherein outputting comprises outputting the performance measurement information to a health care accreditation organization.

9. The method of claim 8 wherein the health care accreditation organization accredits at least one of hospitals, ambulatory care facilities, assisted living facilities, behavioral health care facilities, long-term care facilities, office-based surgery facilities, home care providers, laboratories or combinations thereof.

10. The method of claim 1 further comprising:
formulating the query script based on a specified performance measurement category;
wherein querying comprises executing the query to obtain the performance measurement information, at least some of the obtained performance measurement information obtained from the free text.

11. The method of claim 1 wherein querying comprises querying records from a sampled patient population or an entire patient population and wherein outputting comprises outputting a compliance report corresponding to the sampled or entire patient population.

12. The method of claim 1 wherein querying comprises querying as a function of a performance measurement category including one or more of acute myocardial infarction, heart failure, pneumonia, pregnancy, and combinations thereof.

13. The method of claim 1 wherein outputting comprises outputting compliance metrics determined by regulatory organizations.

14. The method of claim 1 wherein outputting comprises outputting a quality of care of a category related to the health care guideline.

15. The method of claim 1 wherein querying comprises querying a sampled patient population.

16. The method of claim 1 wherein querying comprises querying an entire patient population for a performance measurement category.

17. The method of claim 1 wherein outputting comprises outputting to a health care provider.

18. The method of claim 1 wherein querying comprises querying by a service provider other than healthcare providers.

19. The method of claim 1 wherein outputting comprises outputting via the Internet.

20. The method of claim 1 wherein querying comprises querying at a health care accreditation organization.

21. The method of claim 1 wherein outputting comprises outputting probabilistic information.

22. The method of claim 1 wherein querying comprises determining whether the health care guideline is appropriate for a given patient.

23. The method of claim 1 wherein outputting performance measurement information comprises outputting the performance measurement information by a service provider.

24. The method of claim 1 wherein outputting performance measurement information comprises outputting information for an aspect of health care quality, safety, or compliance with a standard.

25. The method of claim 1 wherein outputting performance measurement information comprises outputting a report, outputting to a magnetic or optical disc, electronically transmitting or displaying on a screen.

26. A method for automatically generating performance measurement information for health care organizations, the method comprising:
mining, with a machine, medical information related to a health care guideline from a computerized patient record;
combining, with the machine, evidence from the mining, the evidence being combined referring to different values of a same variable and being probabilistic such that a probability is provided for each piece of evidence, the probability for each piece of evidence indicating a confidence in the respective value, at least some of the probabilities being less than 100% and greater than 0%, the combined evidence being a unified probability calculated from the probabilities for the evidence, the unified probability being less than 100% and greater than 0%, the combining being pursuant to a mathematical operation such that the unified probability is a numerical value that is based on the probabilities for the evidence applied as input to the mathematical operation;
assigning a final value for the variable as a function of the probabilities for each piece of evidence, the final value being different than the unified probability;
querying with the machine, the machine executing a query script formulated by the machine, a data source having the final value for the combined evidence, the querying based on the health care guideline; and
outputting probabilistic performance measurement information indicating a level of compliance with the health care guideline as a function of the combined evidence.

27. The method of claim 26 further comprising:
calculating an evaluation score of a health care provider from the probabilistic performance measurement information; and
outputting the evaluation score.

28. The method of claim 27 wherein outputting the evaluation scores comprises outputting the evaluation scores to consumers via the Internet.

29. The method of claim 28 wherein outputting the evaluation score comprises outputting a ranking of health care providers.

30. The method of claim 29 wherein outputting the evaluation score comprises ranking the health care providers in different performance measurement categories.

31. The method of claim 26 further comprising:
formulating the query script based on a specified performance measurement category;
wherein querying comprises executing the query to obtain the probabilistic performance measurement information.

32. The method of claim 26 wherein querying comprises querying a plurality of patient records associated with a health care provider and wherein outputting comprises outputting patient information for the health care provider being evaluated.

33. The method of claim 26 wherein querying comprises querying as a function of a performance measurement category including one or more of acute myocardial infarction, heart failure, pneumonia, pregnancy, and combinations thereof.

34. The method of claim 26 wherein outputting comprises outputting the performance measurement information to a health care accreditation organization.

35. The method of claim 26 wherein outputting comprises outputting compliance metrics determined by regulatory organizations.

36. The method of claim 26 wherein outputting comprises outputting a quality of care of a category related to the health care guideline.

37. The method of claim 26 wherein querying comprises querying a sampled patient population.

38. The method of claim 26 wherein querying comprises querying an entire patient population for a performance measurement category.

39. The method of claim 26 wherein outputting comprises outputting to a health care provider.

40. The method of claim 26 wherein querying comprises querying by a service provider other than healthcare providers.

41. The method of claim 26 wherein outputting comprises outputting via the Internet.

42. The method of claim 26 wherein querying comprises querying at a health care accreditation organization.

43. The method of claim 26 wherein the patient records include free text.

44. The method of claim 26 wherein querying comprises determining whether the health care guideline is appropriate for a given patient.

45. The method of claim 26 wherein outputting probabilistic performance information comprises outputting by a service provider.

46. The method of claim 26 wherein outputting performance measurement information comprises outputting information for an aspect of health care quality, safety, or compliance with a standard.

47. The method of claim 26 wherein outputting performance measurement information comprises outputting a report, outputting to a magnetic or optical disc, electronically transmitting or displaying on a screen.

48. A system for automatically generating performance measurement information for health care organizations, the system comprising:
   a machine configured as a data miner, the data miner configured to mine free text for health care data related to a health care guideline for a patient, the free text being stored physician notes, the mining using probabilistic information, the probabilistic information comprising a chance of occurrence for possible values of a variable being mined for the patient, the chances calculated from probabilities assigned to pieces of evidence extracted from the free text for the patient, the probabilities being less than 100% and greater than 0%, the possible value for the variable with the chance of occurrence greater than chances for other possible values for the variable being assigned for the patient, as part of the mining, as the health care data for the variable, and the mining being a function of a health care domain-specific knowledge, the health care domain-specific knowledge associated with the health care guideline, the mining populating a data source with at least some health care data mined from the free text, a structure of the mined data in the data source being different from a structure of the free text so that compliance querying may be performed using the data source, the structure of the mined data in the data source comprising the at least some health care data for the variable separate from the free text;
   the data source having the at least some data populated from the free text; and
   the machine configured to query, by executing a script defining a plurality of constraints and formulated by the machine, the data source, the querying based on health care guideline, and operable to output performance measurement information indicating a level of compliance with the health care guideline based on the querying.

49. The system of claim 48 wherein the machine is operable to query as a function of a specified performance measurement category.

50. The system of claim 48 wherein the data source has a plurality of patient records associated with a health care provider being evaluated and wherein the machine is operable to output a level of compliance for the health care provider being evaluated.

51. The system of claim 48 wherein the machine is operable to output compliance metrics determined by regulatory organizations.

52. The system of claim 48 wherein the performance measurement information is output by a service provider.

53. A system for automatically generating performance measurement information for health care organizations, the system comprising:
   a machine configured as a data miner, the data miner configured to mine a computerized patient record for medical information related to a health care guideline, the mining based on a health care domain-specific knowledge, the health care domain-specific knowledge associated with the health care guideline, and combine evidence from the mining, the evidence being combined referring to different values of a same variable and being probabilistic such that a probability is provided for each piece of evidence, the probability for each piece of evidence indicating a confidence in the respective value, at least some of the probabilities being less than 100% and greater than 0%, the combined evidence being a unified probability calculated from the probabilities for the evidence, the unified probability being less than 100% and greater than 0%, the combining being pursuant to a mathematical operation such that the unified probability is a numerical value that is based on the probabilities for the evidence applied as input to the mathematical operation, the data miner configured to assign an element value for the variable as a function of the probabilities for each piece of evidence, the element value being different than the unified probability;
   a data source having the element value for the combined evidence stored in a tangible media; and
   the machine operable to query the data source, the query being performed by executing a query script formulated by the machine, the querying based on the health care guideline, and operable to output probabilistic performance measurement information indicating a level of compliance with the health care guideline based on the combined evidence.

54. A program storage device readable by a machine, tangibly embodying a program of instructions executable on the machine to perform method steps for automatically generating performance measurement information for health care organizations, the method steps comprising:
   mining, with the machine, free text, the mining of the free text comprising mining for data related to a health care guideline, the mining using medical knowledge, the medical knowledge associated with the health care guideline, the free text being stored physician notes, the mining comprising:
   gleaning, as part of the mining for a patient, a plurality of pieces of evidence about a variable for the patient, at least one of the pieces extracted from the free text;
   using, as part of the mining, probabilistic information, the probabilistic information comprising chances of occurrence for possible values of the variable being mined for the patient, the possible values being derived from the pieces of evidence such that a plurality of possible values and respective chances are provided for the variable;
   calculating, as part of the mining, the chances from probabilities assigned to the pieces of evidence from the free text for the patient, the probabilities being less than 100% and greater than 0%;
   as part of the mining, assigning, as the health care data for the variable for the patient, a value for the variable with the chance of occurrence greater than the chances of other possible values for the variable, the value being different than the respective chance;
   populating a data source with at least some data mined from the free text, a structure of the mined data in the data source being different from a structure of the free text from which the data is mined, the more structure comprising the variable separate from the free text;

querying, with the machine, by executing a query script defining a plurality of constraints and formulated by the machine, a data source having the at least some data populated from the free text representing physician notes, the querying based on the health care guideline; and outputting, by the machine, performance measurement information indicating a level of compliance with the health care guideline based on the querying.

55. A program storage device readable by a machine, tangibly embodying a program of instructions executable on the machine to perform method steps for automatically generating performance measurement information for health care organizations, the method steps comprising:

mining, with the machine, medical information related to a health care guideline from a computerized patient record, the mining based on a health care domain-specific knowledge, the health care domain-specific knowledge associated with the health care guideline;

combining, with the machine, evidence from the mining, the evidence being combined referring to different values of a same variable and being probabilistic such that a probability is provided for each piece of evidence, the probability for each piece of evidence indicating a confidence in the respective value, at least some of the probabilities being less than 100% and greater than 0%, the combined evidence being a unified probability calculated from the probabilities for the evidence, the unified probability being less than 100% and greater than 0%, the combining being pursuant to a mathematical operation such that the unified probability is a numerical value that is based on the probabilities for the evidence applied as input to the mathematical operation;

assigning an element value for the variable as a function of the probabilities for each piece of evidence, the element value being different than the unified probability;

querying, with the machine, the machine executing a query script formulated by the machine, a data source having the element value for the combined evidence, the querying based on the health care guideline; and outputting, by the machine, probabilistic performance measurement information indicating a level of compliance with the health care guideline based on the combined evidence.

56. A method for automatically generating performance measurement information for health care organizations, the method comprising:

extracting, with a machine, multiple pieces of evidence for each variable of a plurality of variables for a first patient, at least one of the pieces of evidence extracted from free text for the first patient based on a domain-knowledge base;

assigning, with the machine, a degree of confidence to each of the pieces of evidence, at least one of the degrees of confidence for each variable being greater than 0% and less than 100%, the degrees of confidence each indicating relative probability of at least two different values for the variable;

combining, with the machine, the degrees of confidence for the multiple pieces of evidence for each variable into a unified probability;

assigning, with the machine, one of the different values of each of the variables as a function of the respective unified probability;

repeating the extracting, assigning the degree of confidence, combining, and assigning one of the different values for a plurality of other patients;

storing in a computerize patient record the assigned ones of the different values for each of the variables for each of the patients;

querying the computerized patient record for each of the patients based on the health care guideline; and outputting performance measurement information indicating a level of compliance with the health care guideline across a patient population of the patients based on the querying.

* * * * *